United States Patent [19]
Hamman

[11] Patent No.: US 6,187,008 B1
[45] Date of Patent: Feb. 13, 2001

[54] DEVICE FOR TEMPORARILY FIXING BONES

[75] Inventor: Gary T Hamman, Warsaw, IN (US)

[73] Assignee: Bristol-Myers Squibb, New York, NY (US)

[*] Notice: Under 35 U.S.C. 154(b), the term of this patent shall be extended for 0 days.

[21] Appl. No.: 09/349,303

[22] Filed: Jul. 7, 1999

[51] Int. Cl.[7] ................................................ A61B 17/56
[52] U.S. Cl. ..................................... 606/72; 606/232
[58] Field of Search .............................. 606/72, 60, 61, 606/62, 64, 70–80, 232

[56] References Cited

U.S. PATENT DOCUMENTS

| 3,463,158 | 8/1969 | Schmitt et al. | 128/334 |
| 3,805,775 | 4/1974 | Fischer et al. | 128/92 |
| 4,091,806 | 5/1978 | Aginsky | 128/92 |
| 4,338,926 | 7/1982 | Kummer et al. | 128/92 |

(List continued on next page.)

OTHER PUBLICATIONS

Reconstructive Surgery of the Joints, Bernard F. Morrey, M.D., Second Edition vol. 1.
Flynn's Hand Surgery, Jesse B. Jupiter, Fourth Edition.
Bioabsorbable. That's the idea behind the new Biofix System, from Acufex. Dec. 1990 JBJS.
Tampering Makes Us Pin Perfect. OrthoSorb, Johnson & Johnson Orthopaedics, Feb. 1991 JBJS.

Primary Examiner—Michael H. Thaler
Assistant Examiner—Len Ngo

(57) ABSTRACT

An implant has a threaded end for screwing into a bone on one side of a joint and an extending resorbable polymer shaft for crossing the joint. The resorbable shaft is fixed in a bone on the opposite side of the joint. The present invention avoids joint stiffness by allowing slight movement of the bones relative to one another initially while the soft tissues heal. As the shaft resorbs, it allows progressively more motion in the joint so that the articular surfaces are not degraded from lack of motion. Eventually, the shaft is completely resorbed thus requiring no removal operation. The implant of the present invention also finds application in bridging a bone fracture to allow progressive load shifting to the bone during healing.

5 Claims, 3 Drawing Sheets

U.S. PATENT DOCUMENTS

| | | | |
|---|---|---|---|
| 4,388,921 | 6/1983 | Sutter et al. ............................ | 128/92 |
| 4,414,967 | 11/1983 | Shapiro ................................. | 128/92 |
| 4,492,226 | 1/1985 | Belykh et al. ......................... | 128/92 |
| 4,632,100 | 12/1986 | Somers et al. ......................... | 128/92 |
| 4,756,307 | 7/1988 | Crowninshield ....................... | 128/92 |
| 4,776,329 | 10/1988 | Treharne ................................ | 128/92 |
| 4,790,304 | 12/1988 | Rosenberg ............................. | 128/92 |
| 4,858,603 | 8/1989 | Clemow et al. ........................ | 128/92 |
| 4,898,186 | 2/1990 | Ikada et al. ............................ | 606/62 |
| 4,905,680 | 3/1990 | Tunc ..................................... | 606/69 |
| 4,944,742 | 7/1990 | Clemow et al. ........................ | 606/59 |
| 4,990,161 | 2/1991 | Kampner ............................... | 623/16 |
| 5,053,035 | 10/1991 | McLaren ................................ | 606/67 |
| 5,057,110 | 10/1991 | Kranz et al. ........................... | 606/62 |
| 5,084,051 | 1/1992 | Törmälä et al. ........................ | 606/77 |
| 5,129,904 | 7/1992 | Illi ........................................ | 606/72 |
| 5,129,906 | 7/1992 | Ross et al. ............................. | 606/77 |
| 5,152,765 | 10/1992 | Ross et al. ............................. | 606/99 |
| 5,169,400 | 12/1992 | Mühling et al. ........................ | 606/73 |
| 5,197,966 | 3/1993 | Sommerkamp ........................ | 606/69 |
| 5,201,738 | 4/1993 | Scott et al. ............................. | 606/77 |
| 5,203,784 | 4/1993 | Ross et al. ............................. | 606/104 |
| 5,207,712 | 5/1993 | Cohen .................................... | 623/21 |
| 5,246,440 | 9/1993 | Ross et al. ............................. | 606/53 |
| 5,380,334 | 1/1995 | Torrie et al. ........................... | 606/104 |
| 5,387,214 | 2/1995 | Kropf et al. ............................ | 606/64 |
| 5,425,776 | 6/1995 | Cohen .................................... | 623/21 |
| 5,431,652 | 7/1995 | Shimamoto et al. ................... | 606/76 |
| 5,458,653 | 10/1995 | Davidson ............................... | 623/23 |
| 5,464,427 | 11/1995 | Curtis et al. ........................... | 606/232 |
| 5,470,334 | 11/1995 | Ross et al. ............................. | 606/72 |
| 5,480,403 | 1/1996 | Lee et al. ............................... | 606/72 |
| 5,486,197 * | 1/1996 | Le et al. ................................. | 606/232 |
| 5,522,817 | 6/1996 | Sander et al. .......................... | 606/72 |
| 5,571,193 | 11/1996 | Kampner ............................... | 623/18 |
| 5,584,836 | 12/1996 | Ballintyn et al. ...................... | 606/73 |
| 5,607,427 | 3/1997 | Tschakaloff ............................ | 606/69 |
| 5,634,926 | 6/1997 | Jobe ....................................... | 606/69 |
| 5,643,321 | 7/1997 | McDevitt ............................... | 606/232 |
| 5,681,353 | 10/1997 | Li et al. ................................. | 623/18 |
| 5,695,497 | 12/1997 | Stahelin ................................. | 606/73 |
| 5,725,590 | 3/1998 | Maumy et al. ......................... | 623/22 |
| 5,733,338 | 3/1998 | Kampner ............................... | 623/16 |
| 5,735,901 | 4/1998 | Maumy et al. ......................... | 623/18 |
| 6,096,060 * | 8/2000 | Fitts et al. .............................. | 606/232 |

\* cited by examiner

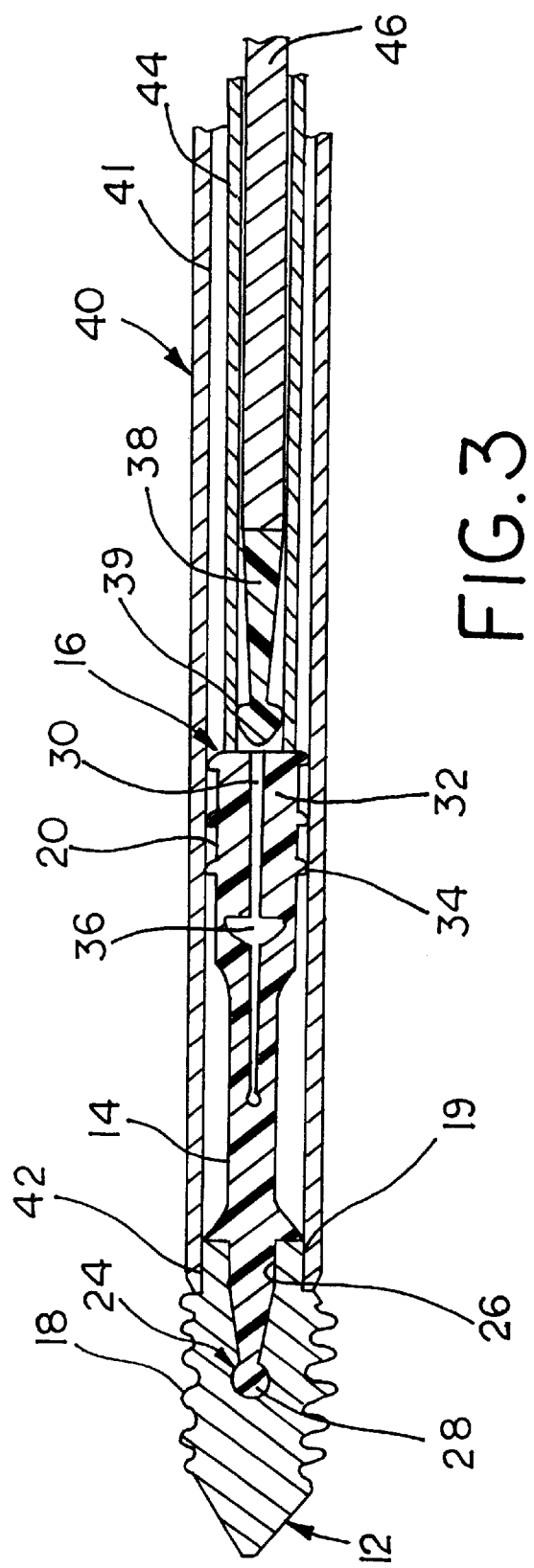

DEVICE FOR TEMPORARILY FIXING BONES

BACKGROUND OF THE INVENTION

The present invention relates to a device for temporarily maintaining the alignment between adjacent body tissues or tissue fragments. More particularly, the present invention relates to a device having a resorbable portion for bridging a bone joint or fracture.

Skeletal injuries often involve the fracture of a bone or the stretching or tearing of soft tissues near a skeletal joint. In either case, it is often necessary to stabilize the fracture or joint in order for the bone or soft tissue to heal. For example, it is common with a wrist injury for the scaphoid and lunate bones to become separated and the ligaments connecting them to become stretched or torn. Initial treatment typically consists of casting the wrist joint to immobilize the bones to permit the soft tissues to heal. When casting fails, surgical intervention is required. This surgery involves inserting screws or wires across the scapholunate joint to immobilize the joint during healing. This procedure results in a stiff joint and potential reoperation to remove the screws and wires.

SUMMARY OF THE INVENTION

The present invention avoids these complications by providing an implant having a threaded end for screwing into a bone on one side of the joint and an extending resorbable polymer shaft for crossing the joint. The resorbable shaft is fixed in a bone on the opposite side of the joint. The present invention avoids joint stiffness by allowing slight movement of the bones relative to one another initially while the soft tissues heal. As the shaft resorbs, it allows progressively more motion in the joint so that the articular surfaces are not degraded from lack of motion. Eventually, the shaft is completely resorbed thus requiring no removal operation. The implant of the present invention also finds application in bridging a bone fracture to allow progressive load shifting to the bone during healing.

BRIEF DESCRIPTION OF THE DRAWINGS

FIG. 3 is a cross sectional view of the distal portion of the assembly of FIG. 2.

DETAILED DESCRIPTION OF THE INVENTION

Figure 1:
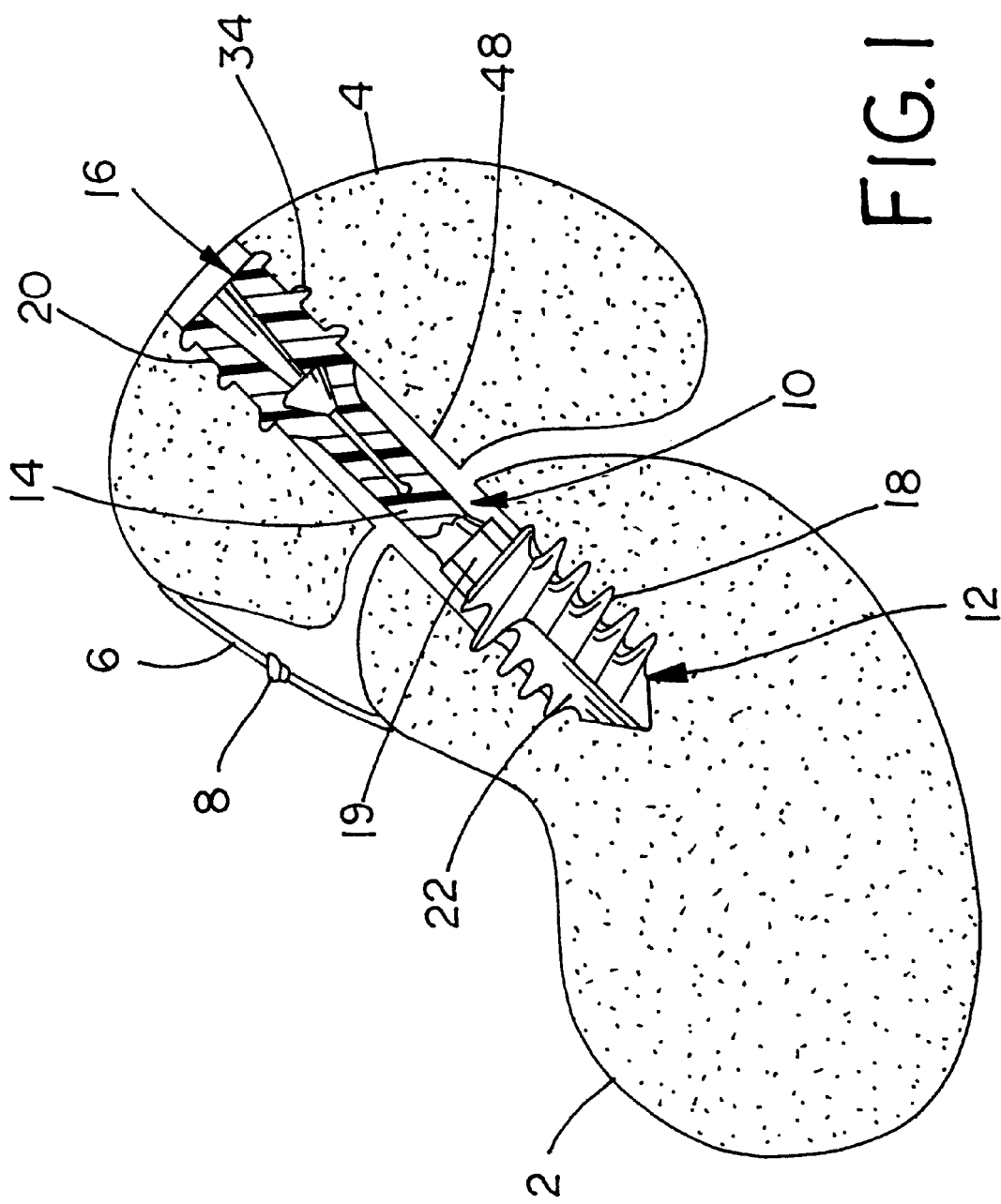
FIG. 1 is a partial cross sectional view of the scapholunate joint immobilized by an implant according to the present invention.

FIG. 1 depicts an exemplary surgical application of the implant of the present invention. The scapholunate joint of the wrist comprises the scaphoid 2 bone, lunate 4 bone, and a ligament 6 joining them. The ligament 6 has sustained an injury and repair 8. An implant 10 according to the present invention connects the two bones to protect the ligament 6 while it heals.

Figure 2:
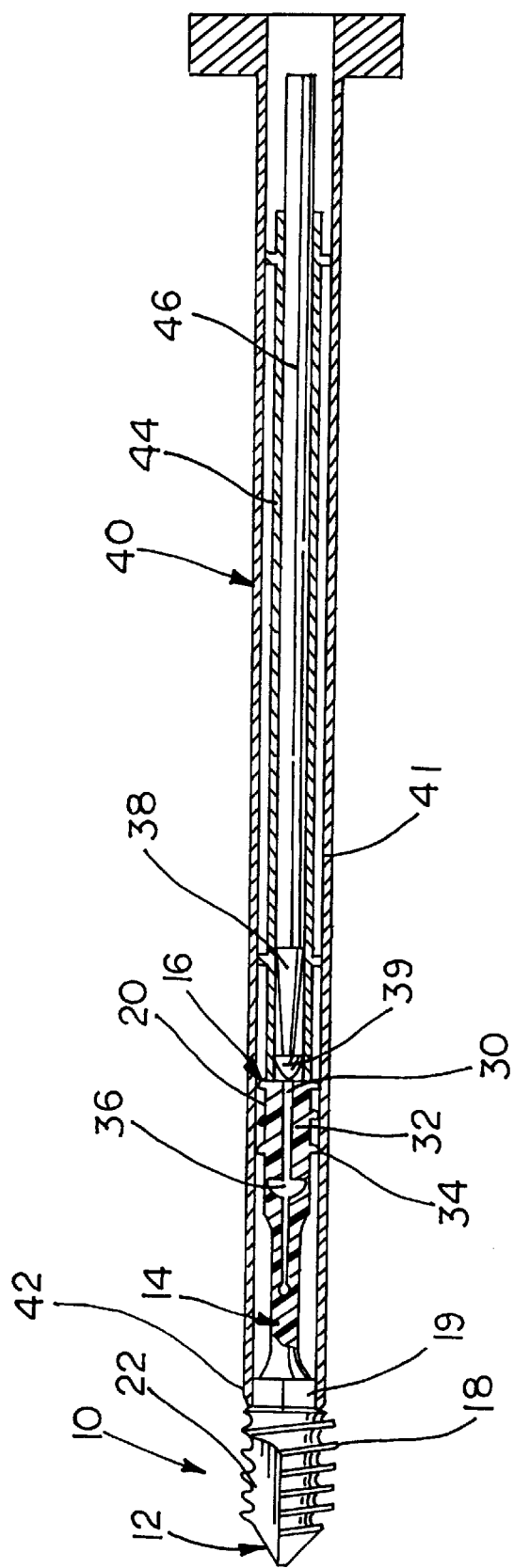
FIG. 2 is a partial cross sectional view of the implant of FIG. 1 assembled with an associated insertion instrument according to the present invention.

FIGS. 1–3 depict an implant and insertion instrument according to the present invention. The implant 10 comprises a leading end 12, a shaft 14, and a trailing end 16. The leading end 12 includes a screw thread 18 and a driver engagement portion 19. The driver engagement portion preferably includes hexagonally arranged driving surfaces. The trailing end 16 includes an expanding portion 20. The implant can be a unitary piece made of a single material. Resorbable polymers are advantageously used to provide progressively more tissue loading and/or motion in the area surrounding the implant. The load transfer or polymer resorption rate can be regulated by the resorbable polymer material choice and implant shaft diameter. Preferably, the leading end 12 is made of a hard material such as metal and the shaft 14 and trailing end 16 are made of resorbable polymer as more clearly shown in FIG. 3. A metal leading end 12 can have both threads 18 and self-tapping flutes 22 so that it can be aggressively driven into a bone without the need for prior tapping of a female thread into the bone. The resorbable shaft 14 is mechanically joined to the leading end 12 to form a positive joint 24 between them. A longitudinal bore 26 is formed in the leading end 12 along the driving axis of the leading end 12. A cross hole 28 intersects the longitudinal bore 26. The shaft 14 is molded adjacent the leading end 12 such that the shaft material flows into the bores 26 and 28. When the shaft 14 has hardened, it is mechanically fixed such that it cannot be withdrawn from the leading end 12 without breaking the shaft 14. The trailing end 16 includes an expanding portion 20. The expanding portion 20 includes a slot 30. Preferably the expanding portion 20 includes two intersecting slots 30 extending through the trailing end 16 to form four petals 32. The petals 32 flex outwardly to expand the trailing end 16. Preferably, the petals 32 include barbs 34 that bite into surrounding tissue when the petals 32 are flexed outwardly. A seat 36 is formed adjacent the slots 30 inboard from the trailing end 16. A wedge 38 with an enlarged head 39 is shaped to slide along the slots 30 causing the petals 32 to flex outwardly. The enlarged head 39 snap fits into the seat 36 to retain the wedge in the slots 30 and thus retain the petals 32 in the outwardly flexed position.

An inserter instrument 40 comprises a first elongated tube 41 having a driving portion 42. When the implant 10 is assembled with the inserter instrument 40, the driving portion 42 engages the driver engagement portion 19 of the leading end 12. The shaft 14 and trailing end 16 fit within the interior of the tube 41. A second elongated tube 44 is coaxial with the first tube 41 and fits within the first tube. The second tube 44 contains the wedge 38 and guides it toward the slots 30. A wedge tamp 46 fits inside of the second tube 44 behind the wedge 38.

In use, the bones, or bone fragments, are aligned and a hole 48 is drilled through the near bone and into the far bone. The implant/inserter assembly is threaded into the hole until the leading end 12 is well seated in the far bone. The first tube 41 is withdrawn and the wedge tamp 46 is advanced to drive the wedge 38 into the slots 30 causing the petals 32 to flex outwardly and the barbs 34 to grip the adjacent bone. The head 39 snaps into the seat 36 to retain the wedge 38. As shown in FIG. 1, the implant stabilizes the two bones initially allowing the soft tissue to heal. As the shaft 14 resorbs, relative motion between the bones is gradually increased so that the soft tissue is gradually returned to the normal loading condition. In the case of a bone fracture, the implant stabilizes the fracture initially with subsequent gradual load transfer back to the bone as the fracture heals.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. An orthopaedic implant having a leading end for gripping bone, a trailing end for gripping bone, and an intermediate portion connecting the leading and trailing ends, the intermediate portion being resorbable in the human body, the trailing end being expandable and including a slot defining petals, the slot receiving a wedge to flex the petals outwardly, the petals including barbs facing outwardly, the wedge including an enlarged head and the slot including a seat, the head and seat forming a snap fit.

2. An orthopaedic implant having a leading end for gripping bone, a trailing end for gripping bone, and an intermediate portion connecting the leading and trailing ends, the intermediate portion being resorbable in the human body, the leading end including a permanently affixed hard tip, the tip including threads, the trailing end including a slot defining petals and further including a wedge receivable in the slot to flex the petals outwardly, the implant further including a tubular inserter having a driving portion at an end thereof, the implant leading end including a driver engaging portion in engagement with the driving portion, the implant intermediate portion, trailing end, and wedge lying within the tubular inserter with the wedge directed toward the slot.

3. The implant of claim 2 including a wedge tamp lying within the tubular inserter and adjacent to and directed toward the wedge.

4. A method for temporarily stabilizing a joint in the human body having first and second adjacent articulating bones and supporting soft tissue, the method comprising the steps of:

providing an implant having a leading end for gripping bone, a trailing end for gripping bone, and an intermediate portion connecting the leading and trailing ends, the intermediate portion being resorbable in the human body;

drilling a hole through the first bone mass and into the second bone mass;

inserting the leading end of the implant through the first bone and adjacent the second bone to grip the second bone with the intermediate portion bridging the first and second adjacent articulating bones and the trailing end lying adjacent the first bone;

causing the trailing end to grip the first bone so that the intermediate portion stabilizes the two adjacent articulating bones; and allowing the intermediate portion to resorb over time to gradually increase the relative motion between the two adjacent articulating bones so that the articular surfaces are not degraded from lack of motion.

5. The method of claim 4 further comprising the steps of:

screwing the leading end into the second bone;

expanding the trailing end inside of the first bone; and operatively repairing the soft tissue.

* * * * *